(12) United States Patent
Marino (10) Patent No.: US 11,629,366 B2
(45) Date of Patent: Apr. 18, 2023

(54) METHOD FOR SELECTIVE TRANSLATION OF DESIRED PROTEINS IN THE PRESENCE OF A SPECIFIED NUCLEIC ACID LIGAND

(71) Applicant: Collin Frank Marino, Greenwich, CT (US)

(72) Inventor: Collin Frank Marino, Greenwich, CT (US)

( * ) Notice: Subject to any disclaimer, the term of this patent is extended or adjusted under 35 U.S.C. 154(b) by 809 days.

(21) Appl. No.: 16/290,725

(22) Filed: Mar. 1, 2019

(65) Prior Publication Data

US 2020/0080126 A1  Mar. 12, 2020

Related U.S. Application Data

(60) Provisional application No. 62/637,377, filed on Mar. 1, 2018.

(51) Int. Cl.
| | |
|---|---|
| *C12P 21/02* | (2006.01) |
| *C12N 9/22* | (2006.01) |
| *C12N 15/11* | (2006.01) |
| *C12N 15/113* | (2010.01) |

(52) U.S. Cl.
CPC .............. *C12P 21/02* (2013.01); *C12N 9/22* (2013.01); *C12N 15/111* (2013.01); *C12N 15/113* (2013.01); *C12N 2310/127* (2013.01); *C12N 2310/128* (2013.01); *C12Q 2521/345* (2013.01)

(58) Field of Classification Search
None
See application file for complete search history.

(56) References Cited

U.S. PATENT DOCUMENTS

| | | | |
|---|---|---|---|
| 2011/0143338 A1* | 6/2011 | Todd ................... | C12Q 1/6816 435/6.1 |
| 2015/0050656 A1* | 2/2015 | Todd ................... | C12Q 1/6818 435/6.12 |

FOREIGN PATENT DOCUMENTS

| | | |
|---|---|---|
| WO | 2008/122084 A1 | 10/2008 |
| WO | 2008122084 A1 | 10/2008 |

OTHER PUBLICATIONS

Scheitl et al. Molecules 25, 3650, pp. 1-14 (Year: 2020).*
Jackson et al.; "The Mechanism of Eukaryotic Translation Initiation and Principles of its Regulation", Nature Reviews/Molecular Cell Biology, vol. 10, Feb. 2010, pp. 113-127.
Mokany et al.; "MNAzymes, a Versatile New Class of Nucleic Acid Enzymes That Can Function as Biosensors and Molecular Switches"; J. Am. Chem. Society, 2010, 132, pp. 1051-1059.
Purtha et al.; "General Deoxyribozyme-Catalyzed Synthesis of Native 3'-5' RNA Linkages", J. Am. Chem. Soc. 2005, 127, pp. 13124-13125.
Ponce-Salvatierra et al.; "Crystal Structure of a DNA Catalyst"; Nature 00 Month 2015, vol. 000, pp. 1-4.
Purtha, Whitney E.; et al.; "General Deoxyribozyme-Catalyzed Synthesis of Native 3'-5' RNA Linkages"; JACS Articles: Journal of the American Chemical Society, vol. 127, No. 38; Sep. 3, 2005; 2 Pages.
Mokany, Elisa, et al.; "MNAzymes, a Versatile New Class of Nucleic Acid Enzymes That Can Function as Biosensors and Molecular Switches"; JACS Articles: Journal of the American Chemical Society, vol. 132, No. 3; Dec. 28, 2009; 9 Pages.
Ponce-Salvatierra, Almudena, et al.; "Crystal Structure of a DNA Catalyst"; Nature, vol. 529; Jan. 6, 2016; 12 Pages.

* cited by examiner

*Primary Examiner* — Brian Whiteman
(74) *Attorney, Agent, or Firm* — Whitmyer IP Group (57) ABSTRACT

There is a method for selective translation of a desired protein. The method has the steps of (a) providing a modified nucleic acid enzyme, including two half cores of a minimized 9DB1 deoxyribozyme split between nucleotides 35 and 39, wherein each half core includes a pendant assembly arm of a strand of nucleic acids extending therefrom and a separate, pendant binding arm extending therefrom of a strand of nucleic acids; (b) binding a nucleic acid ligand to each of the two assembly arms to form an intermediate; (c) binding the intermediate to (i) a first substrate of ribonucleic acid sequences capped at one end, (ii) a second substrate of a strand of ribonucleic acids having a 5' triphosphate region at one end and a region of polyadenylated nucleotides at the other end and wherein the second substrate codes for the desired protein, (iii) join the two half cores to form a core in order to form a ligated product; and (d) allowing the translation for the desired protein to proceed from the ligated product. There is another method for selective translation of a desired protein. There is also a modified nucleic acid enzyme.

3 Claims, 6 Drawing Sheets
(3 of 6 Drawing Sheet(s) Filed in Color)
Specification includes a Sequence Listing.

| SEQ ID NO | Description | 5'-Sequence-3' |
|---|---|---|
| 1 | Forward Primer 1 | TTG GAC CCT CGT ACA GAA GCT AAT ACG |
| 2 | Forward Primer 2 | TAA TAC GAC TCA CTA TAG AGT AAG AAG AAA TAT CAC CA |
| 3 | Reverse Primer | CTT CCT ACT CAG GCT TTA TTC AAA GAC CA |
| 4 | 5' Substrate Template | TAA TAC GAC TCA CTA TAG GGA AAT AAG AGA GAA AAG AA |
| 5 | 5' Substrate Template Complement | TTC TTT TCT CTC TTA TTT CCC TAT AGT GAG TCG TAT TA |
| 6 | Control Ligand Template | TAA TAC GAC TCA CTA TAG GGC GGT CAC CCC AGC AGC CGG TGT CTG TGC CCG GGA GAA GCC |
| 7 | Control Ligand Template Complement | GGC TTC TCC CGG GCA CAG ACA CCG GCT GCT GGG GTG ACC GCC CTA TAG TGA GTC GTA TTA |
| 8 | 9DB1 Deoxyribozyme Right Arm | TCT TAT ATT TCT TCT TAC TGG ATC ATA CGG TCG GAG GGG TTT GCC GTG AAA CCG GCT GCT GGG GTG ACC G |
| 9 | 9DB1 Deoxyribozyme Left Arm | GGC TTC TCC CGG GCA CAG ACT TCA TCT TTT CTC TCT TAT |

METHOD FOR SELECTIVE TRANSLATION OF DESIRED PROTEINS IN THE PRESENCE OF A SPECIFIED NUCLEIC ACID LIGAND

REFERENCE TO SEQUENCE LISTINGS SUBMITTED VIA EFS-WEB

The content of the ASCII text file of the sequence listing named SEQUENCE ST25, which is 1.63 kb in size, was created on Oct. 25, 2019 and electronically submitted via EFS-Web herewith, wherein the application is incorporated herewith in its entirety.

BACKGROUND OF THE DISCLOSURE

1. Field of the Disclosure

The present disclosure relates to methods for selective translation of desired proteins. The present disclosure further relates to a modified nucleic acid enzyme.

2. Description of the Prior Art

Nucleic acid enzymes, alternately referred to as MNAzymes, have been disclosed as useful for functioning as biosensors, molecular switches, and nucleic acid detection systems. See "MNAzymes, a Versatile New Class of Nucleic Acid Enzymes That Can Function as Biosensors and Molecular Switches," Mokany, et al., *J. Am. Chem. Soc.*, 2010, 132, pp. 1051-1059 and in PCT Publication WO 2008/122084. 9DB1 deoxyribozyme, a type of nucleic acid enzyme, is disclosed in "General Deoxyribozyme-Catalyzed Synthesis of Native 3'-5' RNA Linkages," Purtha, et al., J. Am. Chem. Soc. 2005, 127, pp. 13124-13125. The crystal structure of 9DB1 deoxyribozyme is disclosed in "Crystal Structure of a DNA Catalyst," Ponce-Salvatierra, et al., *Nature* 00 Month 2015, Vol. 000, pp. 1-4. 9BD1 deoxyribozyme.

While current nucleic acid enzyme systems have been effective in sensory and detection applications to cellular malfunction or genetic abnormality, they have not been effective in effecting a rapid reaction to or remedy for such malfunction or genetic abnormality. It would be desirable to have a nucleic acid enzyme system in which provides such rapid reaction or remedy. It would further be desirable to have a nucleic acid enzyme system which provides rapid protein synthesis in response to cellular malfunction or genetic abnormality.

SUMMARY OF THE DISCLOSURE

According to the present disclosure, there is provided a method for selective translation of a desired protein. The method has the steps of (a) providing a modified nucleic acid enzyme, including two half cores of a minimized 9DB1 deoxyribozyme split between nucleotides 35 and 39, wherein each half core includes a pendant assembly arm of a strand of nucleic acids extending therefrom and a separate, pendant binding arm extending therefrom of a strand of nucleic acids; (b) binding a nucleic acid ligand to each of the two assembly arms to form an intermediate; (c) binding the intermediate to (i) a first substrate of ribonucleic acid sequences capped at one end, (ii) a second substrate of ribonucleic acid sequences having a 5' triphosphate region at one end and a region of polyadenylated nucleotides at the other end and wherein the second substrate codes for the desired protein, (iii) join the two half cores to form a core in order to form a ligated product; and (d) allowing the translation for the desired protein to proceed from the ligated product.

Further according to the present disclosure, there is provided a method for selective translation of a desired protein. The method has the steps of (a) providing a core of a deoxyribozyme, wherein the core has a plurality of pendant binding arms extending therefrom each having a strand of nucleic acids and a pending stem-loop of nucleic acids bound to one of the plurality of binding arms; (b) binding a nucleic acid ligand to the binding arm having the stem-loop so that the stem-loop opens forming an intermediate; (c) binding the intermediate to (i) a first substrate of a strand of ribonucleic acids capped at one end and (ii) a second substrate of a strand of ribonucleic acids having a 5' triphosphate region at one end and a region of polyadenylated nucleotides at the other end and wherein the second substrate codes for the desired protein in order to form a ligated product; and (d) allowing the translation for the desired protein to proceed from the ligated product.

According to the present disclosure, there is provided a modified nucleic acid enzyme. The modified enzyme has a catalytic core of a minimized 9DB1 deoxyribozyme split between nucleotides 35 and 39, two substrate binding arms, and two ligand binding arms extending from a break in the catalytic core.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Embodiments of the present disclosure are described herein with reference to the following figures.

DETAILED DESCRIPTION OF THE DISCLOSURE

An embodiment of a method of the disclosure is to detect a first sequence of genetic code and toggle the translation of another desired sequence (a second sequence) selectively in the presence of the first sequence. The second sequence codes for any protein, which carries out a desired function. The detection of first sequence is carried out by use of a ribozyme or a deoxyribozyme in either of two distinct ways, each of which has characteristic advantages.

One method of detection is to place a stem loop on one or both of pendant arms of a catalytic nucleic acid sequence. The strand of the stem loop is configured to be complementary to the gene sequence desired to be detected, so that when that sequence is present in the target substrate, the stem loop will open up and allow access to the binding arms.

Another method of detection is to cut a catalytic core of the catalytic nucleic acid at a region not essential for catalysis and to add two more binding arms to each side of the cut. This method allows a new core to only assemble in the presence of the desired strand.

Neither of the aforementioned methods have been used to toggle the translation of another protein. If a native 5'-3' ligating deoxyribozyme or ribozyme is used, two sequences of RNA can be ligated together to form a translatable sequence of RNA. There are techniques for carrying this out.

One technique is to ligate the two sections of a start codon together to form either an A→UG ligation or an AU→G ligation. Since the start codon itself is formed by the ligation, this method should work both in vivo and in vitro. However, if an in vivo application is all that is needed, the ligation can occur anywhere in the 5' UTR because the 5' region will be capped and lead to recruitment of elF4F cap binding complex and the 30s ribosomal subunit at the 5' end and start "scanning" down the 5' UTR until it reaches a start codon. Before the ligation occurs, there will be no start codon and so the following step of ribosomal initiation cannot proceed. Furthermore, the binding of the elF4F complex will be enhanced after the ligation has occurred so that the poly(A) tail on the 3' end can loop back and increase the initiation efficiency.

Other techniques are also possible. One is to use an RNA molecule which is branched at its 5' end such that the first nucleotide contains both a native 3'-5' linkage and a 2'-5' linkage. A deoxyribozyme or ribozyme capable of cleaving the 2'-5' linkage could then be used to enable the translation selectively by the same means explained above. Unfortunately, no such deoxyribozymes or ribozymes currently exist and so one would have to be discovered via in vitro selection. Deoxyribozymes like the 10-23, capable of cleaving 5'-3' linkage seem to imply that such a 2'-5' cleaving deoxyribozyme would be possible. Finally, a transplicing deoxyribozyme or ribozyme could also be used, and regulated in the same way as the ligase and phosphodiesterase, to directly steal the cap from a cellular mRNA molecule and lead to the translation of the desired protein in a way similar to the ligation approach but with the benefit that the 5' substrate would not have to be added making it a three-part system, or even two-part if a stem loop is used, instead of a four-part system.

Figure 1:
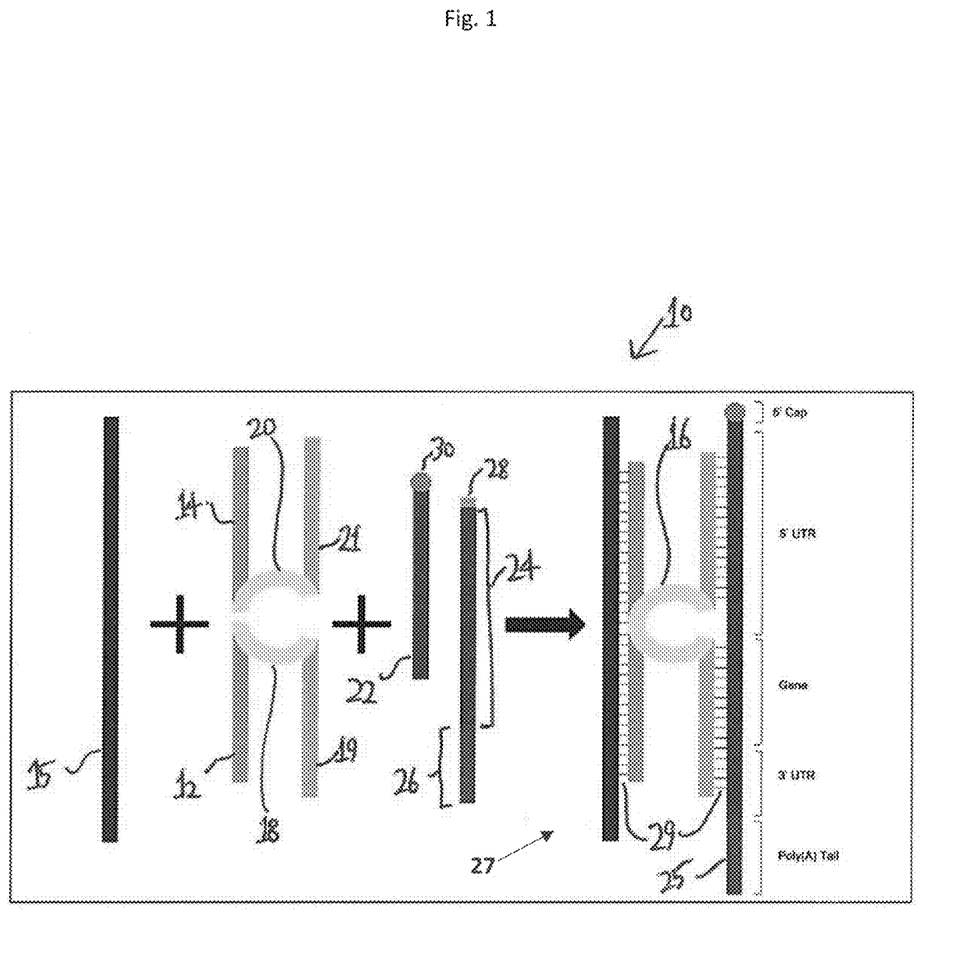
FIG. 1 depicts the operation of an embodiment of a method according to the present disclosure.

FIG. 1 shows the operation of a four-part ligase-based system generally referenced by the numeral 10. Two assembly arms 12 and 14 (light blue) bind the ligand 15 (dark blue) in order to form a functional core 16 from two halves 18 and 20 of the core (yellow). When core 16 assembles, substrates 22 and 24 (dark green) attach binding arms 19 and 21 (light green) and are ligated to form a ligated product 25 (substrate 22 plus substrate 24) and a ligated product complex 27 (the entirety) is then translatable and translation of the protein coded for by the region referred to as the "gene" then takes place. Orange region 28 of substrate 24 represent the 5' triphosphate required for ligation to take place. Poly (A) tail 26 (purple) is a long chain of adenine nucleotides added to substrate 24 during processing or manufacture to increase the stability of the molecule. There are a plurality of chemical/associative bonds 29 that bind ligand 15 to assembly arms 12 and 14 and core 16 and that bind binding arms 19 and 21 to substrates 22 and 24.

Figure 2:
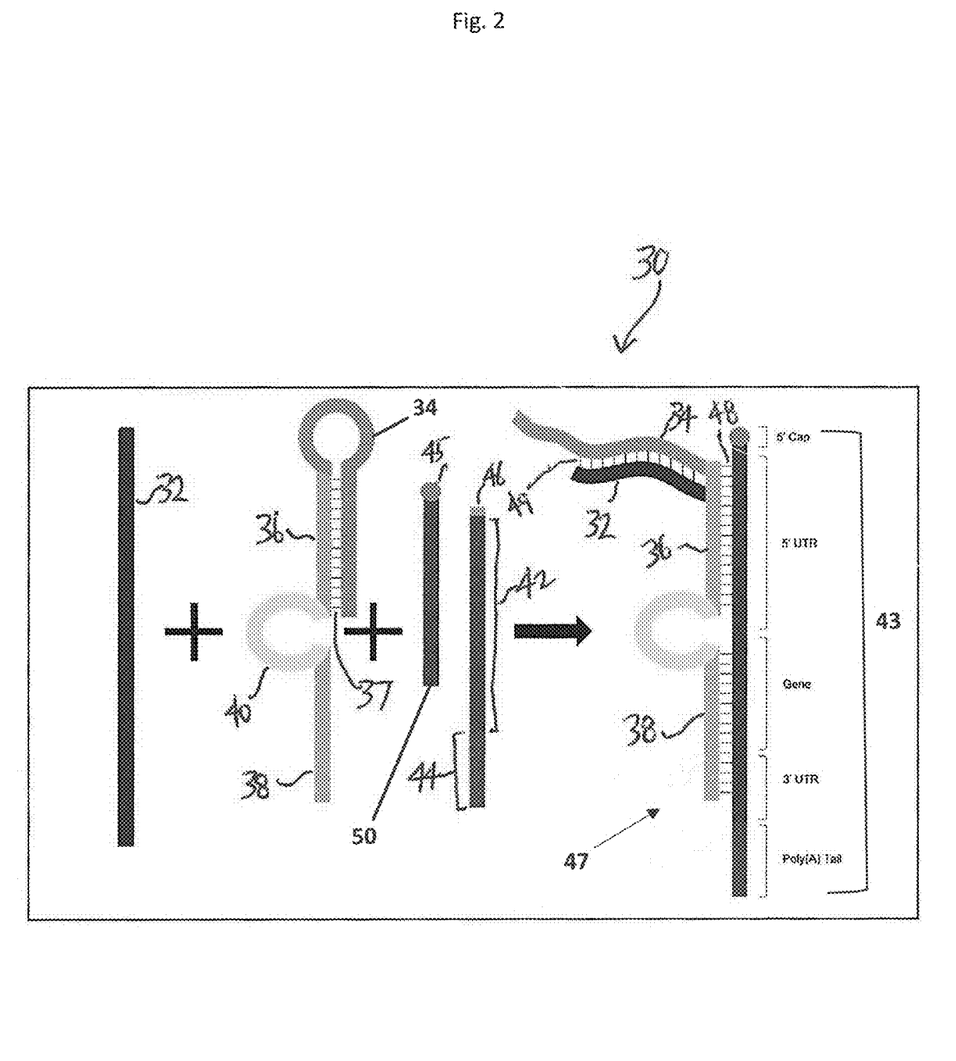
FIG. 2 depicts the operation of another embodiment of a method according to the present disclosure.

FIG. 2 shows the operation of a stem-loop regulated ligase system generally referenced by the numeral 30. A functional core 40 (yellow) has binding arms 36 and 38 (light green) and a stem loop 34 (light blue), which is bound to binding arm 36 via a plurality of chemical/associative bonds 37. Ligand 32 (dark blue) binds to stem loop 34 causing it to open and allows upper substrate 50 (dark green with a red cap 45) to bind to bottom substrate 42 (dark green) to form a ligated product 43 (substrate 50 plus substrate 42) and a ligated product complex 47 (the entirety), which can then be translated. Orange region 46 of bottom substrate 42 represents the 5' triphosphate required for ligation to take place. Poly (A) tail 44 (purple) is a long chain of adenine nucleotides added to substrate 42 during processing or manufacture to increase the stability of the molecule. There are a plurality of chemical/associative bonds 48 that bind binding arms 36 and 38 to ligated product 43 and a plurality of chemical/associative bonds 49 that bind ligand 32 to stem loop 34 (opened).

Figure 3A:
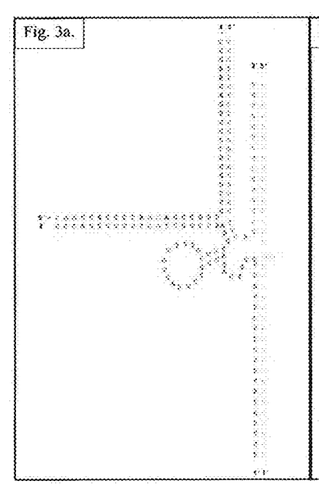
FIG. 3a depicts a secondary structure of a ligase design with a cut core, including SEQ ID NOS 8 and 9 used in the Examples.
Figure 3B:
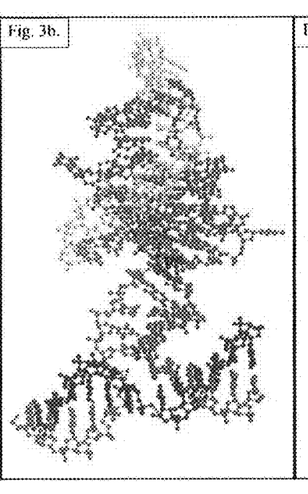
FIG. 3b depicts a proposed crystal structure of a 9DB1 deoxyribose.
Figure 3C:
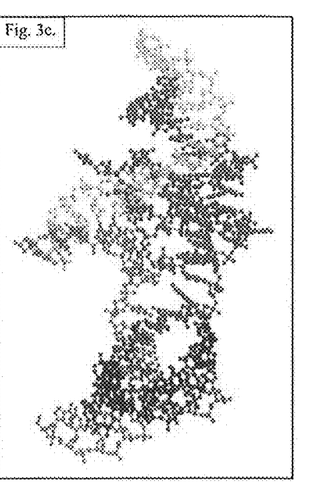
FIG. 3c depicts a slight, clockwise, rotation of the proposed crystal structure of FIG. 3b.

FIGS. 3a to 3c show secondary and tertiary structures of ligase design with a cut core. The ligase shown here is the 9DB1 deoxyribozyme preferred in the present disclosure. Strand colors are consistent throughout. FIG. 3a shows the secondary structure of the system. The red and green strands make up the core. The blue strand is the ligand and the yellow strand is the ligated product. FIG. 3b shows the proposed crystal structure of the 9DB1 deoxyribozyme. The top half of the image is based on the crystallography data for the 9DB1 deoxyribozyme, while the bottom half shows the modification made to allow for the selective catalysis. FIG. 3c shows a slight, clockwise, rotation of the proposed crystal structure FIG. 3B around the vertical axis.

Additional teachings to translation/initiation are shown in "The Mechanism of Eukaryotic Translation Initiation and Principles of its Regulation," Jackson, et al., *Nature Reviews/Molecular Cell Biology*, Vol. 10, February 2010, pp. 113-127.

The modified nucleic acid enzyme has a catalytic core of a minimized 9DB1 deoxyribozyme split between nucleotides 35 and 39, two substrate binding arms, and two ligand binding arms extending from a break in the catalytic core.

Figure 5:
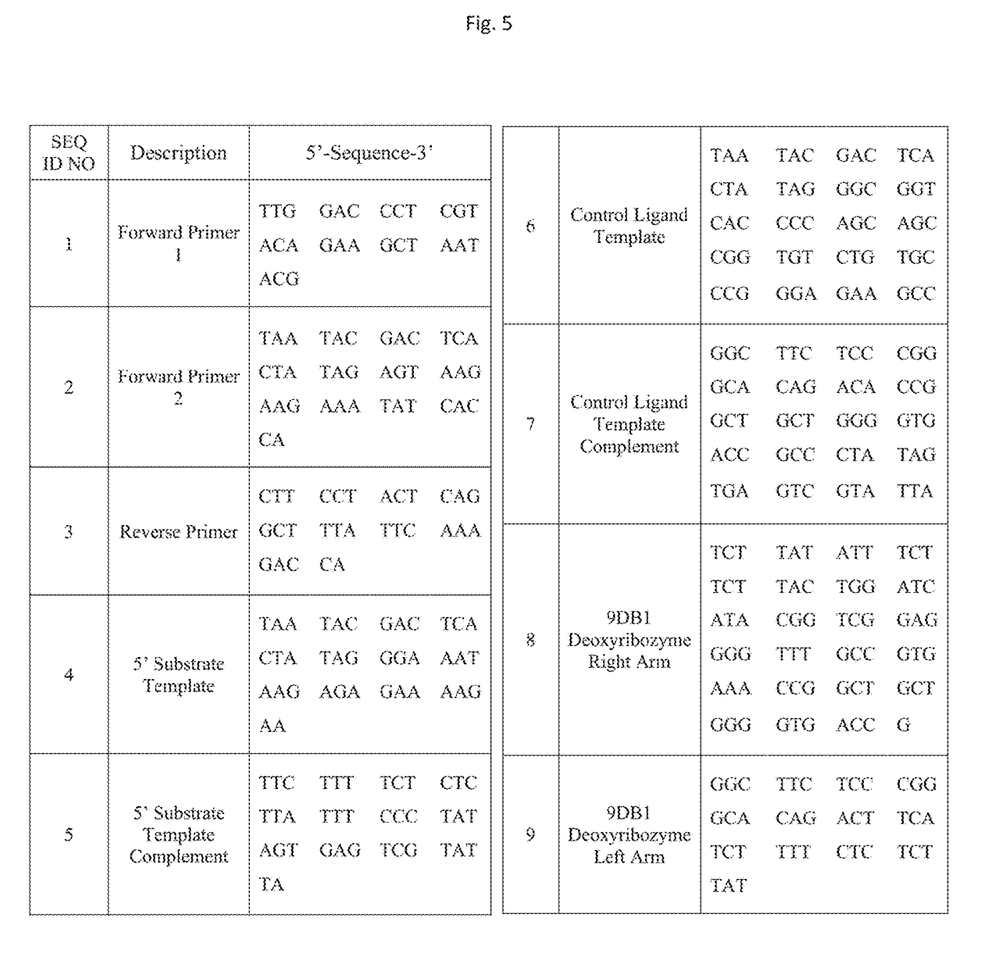
FIG. 5 depicts SEQ ID NOS 1-9 used in the Examples.
Figure 6:
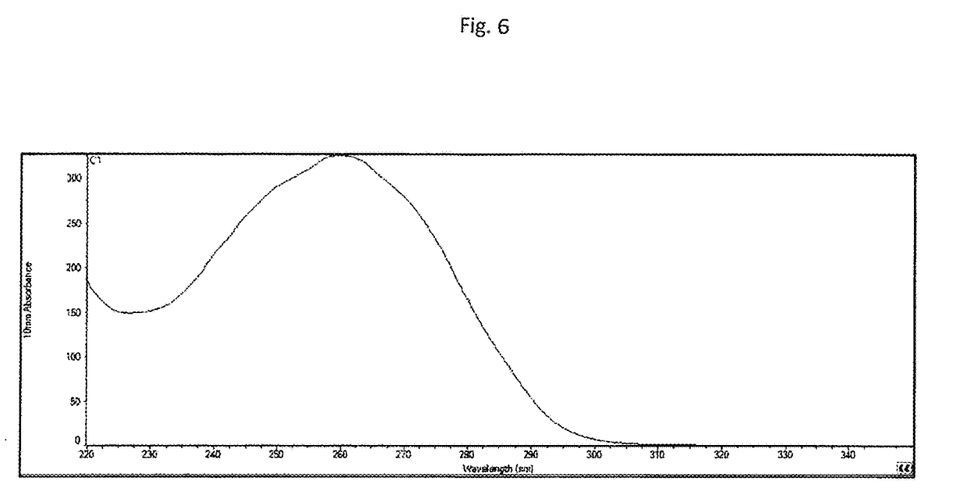
FIG. 6 is a plot an absorbance curve of the mRNA control of the Examples.
Figure 7:
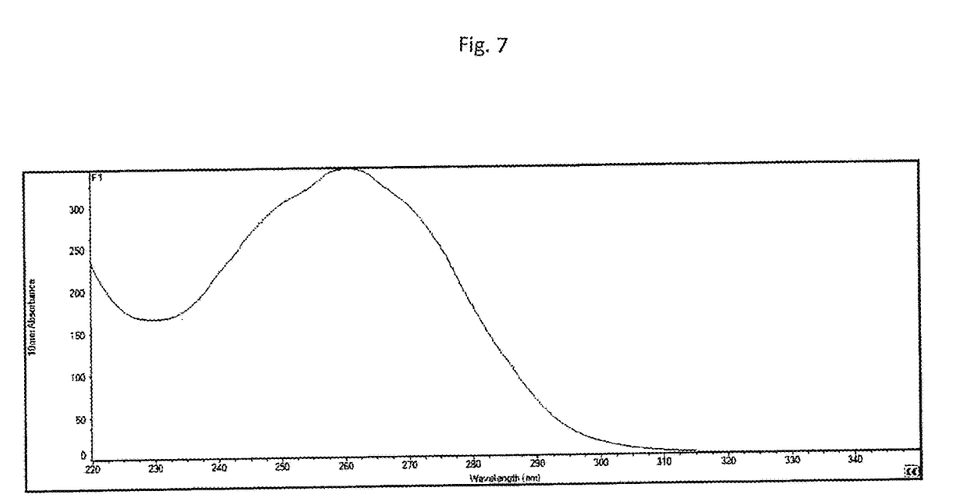
FIG. 7 is a plot an absorbance curve of the 3' Substrate of the Examples.
Figure 8:
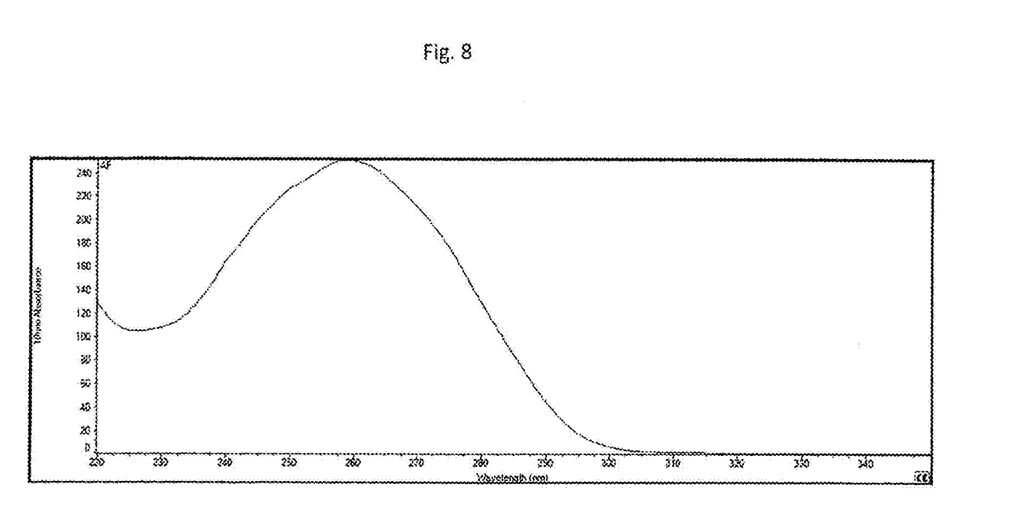
FIG. 8 is a plot an absorbance curve of the RNA ligand of the Examples.
Figure 9:
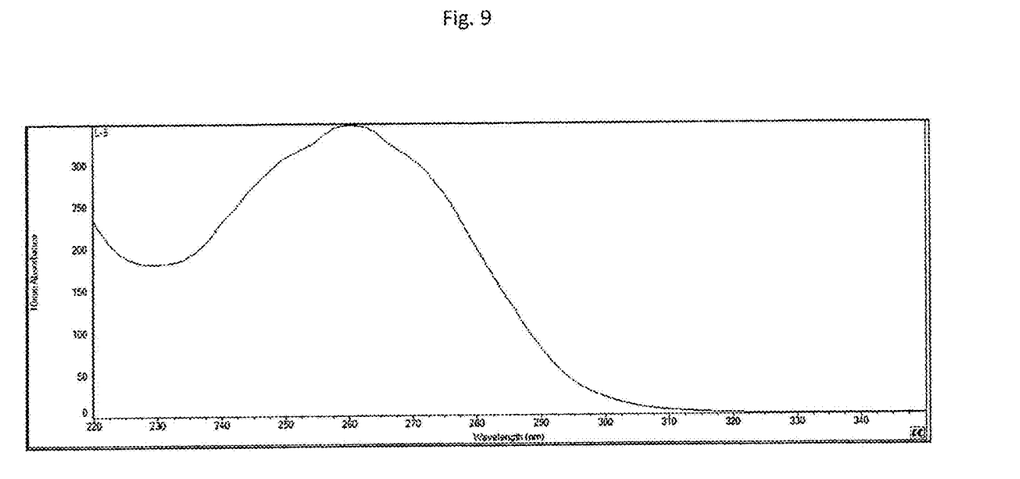
FIG. 9 is a plot an absorbance curve of the 5' Substrate of the Examples.

An example of a split between nucleotides is shown in FIG. 3a, and its sequences, SEQ ID NO 8 and SEQ ID NO 9 are shown in FIG. 5, for the application of detecting hTERT mRNA and ligating GFP mRNA. An example of a more general sequence could be SEQ ID NO: 10
5' . . . N*NNNNNNNNNN*GGATCATACGGTCGGAGGGGTTTGCCGTGAA *NNNNNNNNNN* . . . 3' for one half of the core (exemplified by half core 18 in FIG. 1 and

5' . . . *NNNNNNNNNNN*TTCA*NNNNNNNNNNN* . . . 3' for the other half core (exemplified by half core 20 in FIG. 1). "N" denotes the presence of any nucleic acid (A, T, C or G). Additionally, the central (or bold) regions represent the catalytic core, the underlined regions represent ligand binding arms, and the italicized regions represent substrate binding arms. The ellipses represent that the length of the arms is arbitrary much like their sequence.

There are a numerous end uses for the methods/systems of the present disclosure ranging from nucleic acid detection to cancer treatments. In a cancer treatment, the system would be made to assemble or activate on/in the presence of a mutated piece of mRNA. This would allow the ligation to only occur in the cancerous cells that have this mutation. As a result, the system would have to be customized on a per-patient basis. This entails making either the stem loop or assembly arms complementary to the mutated region of the mRNA depending on the configuration/design used. Then, the ligated product is configured to code for a protein that will lead to the death of the cell. Some ways in which this could be achieved are by translating an intermediate in an apoptosis signaling pathway, translating membrane proteins that flag the cell for attack by the immune system, and translating a deoxyribonuclease that contains a nuclear localization sequence. Another application/end use is in selective antibiotics. In that end use, the system would be configured to detect a region on a bacterial mRNA that is known to only be present in that bacteria species. When the system is activated, you would have the product kill the cell in the same way as the previous system. Yet another end use is in nucleic acid detection systems when a researcher wants to know if there is a certain sequence present in a cell culture. In that end use, the system would be configured to translate a fluorescent protein, such as GFP, in the presence of the sequence for which detection is desired. The system could be easily transfected into the cells, or, alternately, transduced with a virus. Finally, another end use is in regards to autoimmune diseases. In that end use the system would be configured to detect the mRNA which codes for the autoantigen of the disease. When the system is activated, the resulting protein would kill the cell the same as in the cancer end use.

Another embodiment of the present disclosure are nucleic acid enzymes having a catalytic core of a modified 9DB1 deoxyribozyme. The enzymes have one or more strands of ribonucleic acid or deoxyribonucleic acid and a catalytic core of modified 9DB1 deoxyribozyme. Preferred nucleic acid enzymes are the MNAzymes, which are disclosed by way of example in "MNAzymes, a Versatile New Class of Nucleic Acid Enzymes That Can Function as Biosensors and Molecular Switches," Mokany, et al., *J. Am. Chem. Soc.,* 2010, 132, pp. 1051-1059 and in PCT Publication WO 2008/122084. 9DB1 deoxyribozyme and methods for making same are disclosed in "General Deoxyribozyme-Catalyzed Synthesis of Native 3'-5' RNA Linkages," Purtha, et al., *J. Am. Chem. Soc.* 2005, 127, pp. 13124-13125. The crystal structure of 9DB1 deoxyribozyme is disclosed in "Crystal Structure of a DNA Catalyst," Ponce-Salvatierra, et al., *Nature* 00 Month 2015, Vol. 000, pp. 1-4.

The present disclosure is further illustrated herein by the following non-limiting examples.

EXAMPLES

One of the main issues with personalized cancer treatments heretofore has been the diverse nature of cancer. While numerous proto-oncogenes have been identified over the last several years, the specific mutations vary dramatically from case-to-case. This means that in order for a personalized medicine approach to be successful, the patient must have a similar mutation to one which has already been targeted; otherwise, a new treatment would have to be researched, tested and approved for every new case. Desired is a system that could be designed that is easily customizable and that could be modified on a per-patient basis to target any given mutation. With such a system, traditional personalized medicine approaches could be taken, but instead of using the information gathered about the patient's mutations to recommend a treatment, this mutation could be the target of a specialized treatment and would not require any additional research and development. Such a system needs to have two components, a region capable of taking any nucleic acid input and the ability to selectively kill a cell based on its output. Deoxyribozymes could be prime candidates for such a system as they can be modified more easily than proteins, and their ability to detect nucleic acids can vary by even a single nucleotide. A deoxyribozyme-based system could also be capable of killing a cell if it were able to release cytotoxic proteins in the presence of the input. This release mechanism is most easily achieved if a ligase deoxyribozyme, such as a 9DB1 deoxyribozyme, is used to ligate a polyadenylated, protein-coding RNA to a 5'-7-methylguanosine capped RNA. This will result in an RNA molecule that is only translatable after the ligation has occurred, meaning the cells will only be killed if they contain a target region of RNA, a region that could be different in every patient and would not require additional research to be targeted.

Goal

The goal of this example is to show that a selective, deoxyribozyme-based system is capable of detecting a sequence of RNA in living cells and selectively translating a protein in its presence. In order to show that the system functions, green fluorescent protein (GFP) was used in the place of a cytotoxic protein so that a false positive could not be caused by the transfection procedures. Additionally, the system was made to target a region of the human telomerase reverse transcriptase (hTERT) mRNA so that the system could be transfected into HeLa and IMR90 cells, which should be telomerase positive and telomerase negative respectively. This yielded GFP in the HeLa cells, but not the IMR90 cells showing that the system functions in vivo and is capable of determining between a cancerous and a non-cancerous cell line based on the mRNA sequence it was configured to look for. hTERT should never be targeted in a clinical trial as the system would also kill a patient's germ cells. In real applications, a specific mutation would be targeted by changing two of the arms on the deoxyribozyme.

Figure 4:
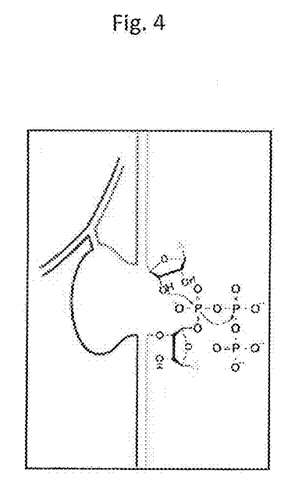
FIG. 4 depicts the mechanism of the condensation reaction when the substrate assembles on the ligand.

The system itself consists of four nucleic acid sequences. The first two sequences are very similar as each consists of a substrate binding region, part of the deoxyribozyme core and a ligand binding region; these two sequences are shown in green and red in FIG. 3*a*. The ligand binding regions allow the system to detect any desired nucleic acid. In the presence of the ligand, they allow the two halves of the deoxyribozyme to be held together so that catalysis can occur. This system-ligand complex is shown in FIGS. 3*a*-3*c*. When the system then assembles on the ligand the 3' and 5' ends of the substrates are brought into close proximity which leads to a condensation reaction between them, the mechanism of which is shown in FIG. 4. This allows ligation to occur selectively in the presence of the ligand. However, the most important aspect of the system is the RNA that is ligated together. The 5' sequence consists of a 5'-7-methylguanosine cap and a 5' untranslated region (UTR), while the 3' substrate consists of the rest of the 5' UTR, a start codon followed by a coding sequence for the desired protein, and a polyadenylated tail. This effectively toggles the translation of the RNA as the coding region cannot initiate with a ribosome in the absence of the capped region. No proteins can be made in the absence of the ligand.

Methodology

Preparation of DNA Templates

Short Template DNA, PCR primers, and deoxyribozyme components were obtained from Integrated DNA technologies. SEQ ID NO 4 and SEQ ID NO 6, (shown in FIG. 5) were annealed with SEQ ID NO 5 and SEQ ID NO 7 respectively. These templates and their transcripts are referred to as the 5' Substrate and the ligand. This was achieved by mixing each sequence at a 1:1 molar ratio, heating to 95° C. for 5 minutes and letting cool until room temperature. Two GFP coding templates also needed to be prepared and so the 3.3 eGFP Plasmid (Addgene, Catalog No. 26822) was obtained from Addgene and sent to Genewiz for purification. Two PCR reactions were then performed to amplify and isolate the desired coding regions. A control sequence was made using SEQ ID NO 1 and SEQ ID NO 3 as the forward and reverse primers respectively. A second sequence was the prepared using the same reverse primer but a downstream forward primer, SEQ ID NO 2, was used instead of SEQ ID NO 1. This forward primer was prepared with its own T7 promoter at its 5' end so that the amplicon would also have the promoter added. The T7 promoter for the control sample, which shall be referred to as the mRNA control in this literature, was already contained in the plasmid. The amplicon which was prepared with SEQ ID NO 2 as its forward primer shall be referred to as the 3' substrate.

FIG. 5 sets forth a table of DNA oligonucleotides used in this example. The number of each sequence is listed along with a description and the sequence data. Sequence numbers are used to refer to the different oligonucleotides. This table contains all of the PCR primers, short DNA templates and deoxyribozyme components used in this research. Table 1 below cross-references sequence # in FIG. 5 with their sequence ID numbers.

TABLE 1

| Sequence # in FIG. 5 | Sequence ID NO |
|---|---|
| 1 | Sequence ID NO: 1 |
| 2 | Sequence ID NO: 2 |
| 3 | Sequence ID NO: 3 |
| 4 | Sequence ID NO: 4 |
| 5 | Sequence ID NO: 5 |
| 6 | Sequence ID NO: 6 |
| 7 | Sequence ID NO: 7 |
| 8 | Sequence ID NO: 8 |
| 9 | Sequence ID NO: 9 |

In Vitro Transcription

The four double stranded templates were then transcribed in vitro using the HiScribe™ T7 High Yield RNA Synthesis Kit according to the given procedures. The mRNA control and the 5' substrate were both transcribed in the presence of m7G(5')ppp(5')G RNA Cap Structure Analog according to the capped transcription procedures also provided by New England Bio Labs. When the reactions had been prepared at the specified concentrations, the mixtures were incubated at 37° C. for 3 hours.

Polyadenylation

After being incubated for 3 hours, two of the samples were put in the freezer for later use. The other two samples, the 3' Substrate and mRNA control, were polyadenylated with E. coli Poly(A) Polymerase. To each 20 µL reaction 2.674 µL 10C E. coli Poly(A) Polymerase reaction buffer (50 mM Tris-HCl, 250 mM NaCl, 10 mM MgCl2 at a pH of 7.9 @ 25° C.), 2.674 µL of 10 mM ATP and 1.334 µL of E. coli Poly(A) polymerase were added. These mixtures were then put back into the incubator and left to sit for one hour at 37° C.

DNase Treatment

After being polyadenylated the samples were treated with DNase 1 to remove the DNA templates. The volume of each sample was increased to 100 µL by the addition of 10× DNase buffer. Note, the 1× buffer (10 mM Tris-HCl, 2.5 mM MgCl2, 0.5 mM $CaCl_2$)) at a pH of 7.6 @ 25° C.) should be used instead, however the reagent was mislabeled and this was not noticed until after it had been used. The samples were then incubated at 10° C. for 10 minutes.

Phenol-Chloroform Purification and Ethanol Extraction

One volume of UltraPure™ Phenol:Chloroform:Isoamyl Alcohol reagent sold by Thermo Fisher was added to each sample. And the mixtures were vortexed for approximately 20 seconds. The samples were then centrifuged for 5 minutes at 16,000×g and the aqueous phase of each sample was transferred to a fresh tube. To each sample 14 of Glycogen (20 µg/µL) was added along with half a volume of 7.5M ammonium acetate and 2.5 volumes of 100% ethanol. Note, that the volume of ethanol is based on the volume of the sample and the volume of the ammonium acetate added. The tubes were then placed in a box of dry ice for one and a half hours and then centrifuged at 4° C. for 30 minutes. The supernatant was removed by careful pipetting and then pellet was washed once more with 150 µL of 70% ethanol. Each sample was then resuspended in 20 µL of nuclease free water.

Preparation of Deoxyribozyme Components

The 9DB1 deoxyribozyme is magnesium ion dependent and forms it secondary structure in a 1:3 DNA:$Mg^{2+}$ ratio. Because the right arm, SEQ ID NO 8, contains all of the regions in which ion-dipole interactions occur this sequence can be annealed in the presence of magnesium chloride prior to transfection. This was achieved by suspending the DNA and magnesium chloride solution so which resulted in a final DNA to $MgCl_2$ ratio of 2:7 to ensure that most of the DNA's tertiary structures formed around the ions. The solution was then heated to 95° C. for 5 minutes to break up any existing structure and left at room temperature until it slowly cooled.

Cell Cultures

HeLa cells and IMR90 cells were taken out of the liquid phase of a nitrogen storage system and added to DMEM containing 10% Fetal Bovine Serum. The cells and medium were then added to a 10 cm culture plate and placed in a cell incubator set to 37° C. for 24 hours. After the cells had adhered to the plates the medium was changed and the plates were put back in the incubator for another 24 hours. Trypsin was then added to the plates and they were left to sit for a few minutes. The medium from each of the two plates was pipetted into its own six-well plate and labeled accordingly. The plates were then put in the incubator and left there until they were ~80% confluent.

Transfection

Lipofectamine 2000 was used to transfect the different system components into the cells. Four samples were prepared in duplicate to serve as the different experimental groups. First 80 of the lipofectamine 2000 reagent was diluted in 1200 µL of Opti-MEM® Medium. Next the different samples were prepared by diluting the appropriate nucleic acids in 700 µL of the Opti-MEM® Medium. Two of these four samples were to serve as positive controls. The first control was made by diluting 44 of a GFP coding plasmid which resulted in a total concentration of around 10 µg/700 µl. The second control was created by adding 5 µg of the control mRNA prepared above. The first experimental group was made to contain 240 µmol of both of the Deoxyribozyme arms. Note that the right arm was annealed with $MgCl_2$ prior to addition as detailed above. This sample also contained 15 µg of both the 5' and 3' RNA substrates. Finally, the fourth sample was prepared in the same way as the third but with the addition of 5 µg of a synthetic RNA ligand to assemble on. These diluted samples were then mixed with the diluted lipofectamine solution in different tubes. The tubes were then left to sit at room temperature for 15 minutes, after adequate mixing with a pipette, so that the DNA-Lipid complexes could form. Finally, the complexes were added to different well plates so that 10 different experimental groups were formed. The groups consisted of two negative controls in which nothing was transfected, two plasmid controls, two mRNA controls, two experimental groups which consisted of just the system and two experimental groups which consisted of the system a synthetic ligand for it to assemble on.

Results
Analysis of RNA Transcripts

The absorbance values of each of the four RNA samples were measured with a NanoDrop in order to measure their concentration and assess their purity. The results are shown in Table 2. The measured 260/280 and 260/230 values showed that all of the samples were extremely pure except for the 5' substrate which was only slightly out of the accepted range. This sample was still pure enough for its use in this experiment and no problems were caused by it.

NanoDrop results are set forth in Table 2. The concentrations and purities of the four RNA sequences are shown. For pure RNA, the 260/280 value should be approximately 2.0 and the 260/230 values should be approximately between 2.0 and 2.2.

TABLE 2

| Sequence | Concentration | A260/A280 | A260/A230 |
| --- | --- | --- | --- |
| mRNA Control | 13,001.1 ng/µL | 1.97 | 2.15 |
| 3' Substrate | 13,742.8 ng/µL | 1.91 | 2.08 |
| Ligand Control | 10,011.7 ng/µL | 1.93 | 2.34 |
| 5' Substrate | 13,784.3 ng/µL | 1.74 | 1.92 |

GFP expression was seen in every sample except for the system alone in the IMR90 cells. These results were exactly as expected and strongly support that the system is functional. The two positive controls showed that the transfection all of the RNA processing steps worked properly. The four samples of interest were Samples 12, 13, 16 and 17. Samples 10 and 11 showed that GFP was expressed in HeLa cells with or without a synthetic ligand present. Whereas Samples 16 and 17 showed that the IMR90 cells were only able to express GFP when the system was transfected with a synthetic ligand. This result strongly implies that the system is only capable of translating proteins when the targeted ligand is present as predicted.

Enzymes are undoubtedly the most important aspect of microbiology. It seems that there are an infinite number of possibilities, however the complexities of protein folding make it almost impossible to engineer a custom enzyme from scratch. If one were able to engineer enzymes with ease, an extremely important design would be for an enzyme which could scan a cell for a given mutation and do something as a result. Such an enzyme would be an enhancement in many disease treatments, including cancer. While this ability is far-fetched, a much more plausible approach is to design a multipart system which is easily modifiable and capable of the same tasks. In this way, a detection method could be coupled to a protein release mechanism and any proteins could be selectively activated in the presence of any nucleic acid. The research which has been performed over the last few years on the mechanisms behind ribosomal initiation, the identification of new catalytic DNA sequences, the crystal structures of said catalytic DNAs and even in vitro detection methods of nucleic acids, have made such a system possible.

Detection mechanisms which are capable of distinguishing between single nucleotide substitutions have been made out of so-called MNAzymes which function by assembling around a specific ligand. These MNAzymes, or Multicomponent Nucleic Acid Enzymes, consist of two pieces, sometimes referred to as Partzymes. Each Partzyme consists of two binding arms and a region of a deoxyribozyme core. One of these binding arms is meant to bind to the substrate, while the other is used to hold the two Partzymes in proximity of one another so that catalysis can selectively occur in the presence of the given ligand, sometimes referred to as an assembly facilitator. The highly specific nature of these newly invented nucleic acid detection systems make them ideal for the input of the system proposed above. The only thing which needs to be shown is that this detection method can be coupled to some sort of protein activation method. This can be achieved by exploiting the way in which mRNA initiates with ribosomes in eukaryotic cells. The key component of efficient translation in living cells is the 5' m7G(5')ppp(5')G cap on the mRNA molecules. To this, the eIF4F complex binds which results in the scanning of the 5' UTR for a start codon. When the AUG codon is reached, it leads to the recruitment of the 40s and 60s ribosomal subunits and the elongation step of translation proceeds. Translation of un-capped mRNAs has been seen to be repressed in living cells showing that this model is fairly accurate and that the cap is crucial for noticeable protein expression. This means that an RNA ligating deoxyribozyme can be used to toggle translation by ligating a capped RNA to a coding RNA as neither sequence can be translated in vivo on its own.

An ideal candidate for this ligation is the 9DB1 deoxyribozyme as it functions in the presence of $Mg^{+2}$ ions around a pH 7.5 and at temperature of 37° C. This makes it ideal for in vivo use as these conditions are almost identical to the ones found in the cytoplasms of most cells. Unfortunately, this deoxyribozyme had not been turned into an MNAzyme heretofore, and so an optimal location had to be identified where the core could be separated. Looking at the crystal structure of this deoxyribozyme, a stretch of 4 nucleotides, 5'-TTTA-3', can be identified between the P3 and P4 regions on a minimized version of the 9DB1. The two thymines in the middle of this sequence do not partake in dipole-dipole interactions with the rest of the core and only function to attach the 3' binding arm to the rest of the core. Furthermore, the original 9DB1 sequence contained a stem loop in this region. In order to make a functional MNAzyme out of the 9DB1 core, the stem of the original hairpin structure was returned, and to it the other two binding arms were added. The proposed crystal structure of this modification is shown in FIGS. 3b and 3c.

In order to show that this modified deoxyribozyme worked in vivo and was capable of selectively expressing a desired protein in the presence of a desired ligand, the system was made to detect hTERT mRNA and translate GFP in its presence. This was tested by transfecting the modified system into both HeLa cells and IMR-90 cells as the HeLa cells have been proven to be telomerase positive, while the IMR-90 cells have been shown to be telomerase negative. As a result, it was expected that the system would result in GFP production only in the HeLa cells as there was no ligand for the modified 9DB1 to assemble on in the IMR-90 cells. It was also expected that if a synthetic ligand was then added to the IMR-90 cells that the system would not have a way to assemble and could once again lead to the production of GFP. Both of these results were seen from the corresponding transfections, and this strongly implies that the system functions as designed.

Now that the system has been shown to function in living cells, it would not be hard to use it to selectively kill cancerous cells; the system can be modified for cancer treatments as follows. The first step in applying the system is to find the mutation which should be targeted. This can be achieved by sequencing regions of the genome, in both the cancerous and healthy cells of the same patient, which are known to contain proto-oncogenes. The sequences are then compared and varying regions are identified. It is expected that there will be numerous mutations between the cells, however if any mutation can be found which is only in the cancerous cells, and not the healthy ones, then the system can be used to selectively kill those cells. It is probable that such—a mutation will exist, as the last proto oncogene mutation to occur before the cell line becomes tumorigenic should not be in any of the healthy cells. After this sequence is identified, the two binding arms can be made complementary to the mutated sequence. Finally, a split piece of mRNA which codes for a cytotoxic protein is prepared in the same way in which the GFP coding 3' Substrate was prepared. There are a large number of proteins that could be chosen, however you do not want neighboring cells to be killed. One proposed method is to translate an intermediate in an apoptosis signaling pathway, or, if the cancer avoids apoptosis, membrane proteins can be translated which cause the cell to be flagged by the immune system of the patient.

The results of the transfection show that the system is capable of detecting cellular sequences of mRNA and translating any desired protein in its presence. In the case of this experiment, hTERT was detected and GFP was translated selectively in its presence. This proves that the mechanism is functional and that other combinations of inputs and outputs can be used with it. There are a large number of applications for this system, one of which is to selectively kill cancerous cells by detecting one of the mutations which lead to the formation of the cancer.

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances which fall within the scope of the appended claims.

SEQUENCE LISTING

<160> NUMBER OF SEQ ID NOS: 10
<210> SEQ ID NO 1
<211> LENGTH: 26
<212> TYPE: DNA
<213> ORGANISM: Homo sapiens
<400> SEQUENCE: 1
ttggacctcg tacagaagct aatacg 26

<210> SEQ ID NO 2
<211> LENGTH: 44
<212> TYPE: DNA
<213> ORGANISM: Homo sapiens
<400> SEQUENCE: 2
taatacgact cactatagag taagaagaaa tataagagcc acca 44

<210> SEQ ID NO 3
<211> LENGTH: 29
<212> TYPE: DNA
<213> ORGANISM: Homo sapiens
<400> SEQUENCE: 3
cttcctactc aggctttatt caaagacca 29

<210> SEQ ID NO 4
<211> LENGTH: 38
<212> TYPE: DNA
<213> ORGANISM: Homo sapiens
<400> SEQUENCE: 4
taatacgact cactataggg aaataagaga gaaaagaa 38

<210> SEQ ID NO 5
<211> LENGTH: 38
<212> TYPE: DNA
<213> ORGANISM: Homo sapiens
<400> SEQUENCE: 5
ttcttttctc tcttatttcc ctatagtgag tcgtatta 38

<210> SEQ ID NO 6
<211> LENGTH: 60
<212> TYPE: DNA
<213> ORGANISM: Homo sapiens
<400> SEQUENCE: 6
taatacgact cactataggg cggtcacccc agcagccggt gtctgtgccc gggagaagcc 60

<210> SEQ ID NO 7
<211> LENGTH: 60
<212> TYPE: DNA
<213> ORGANISM: Homo sapiens
<400> SEQUENCE: 7
ggcttctccc gggcacagac accggctgct ggggtgaccg ccctatagtg agtcgtatta 60

<210> SEQ ID NO 8
<211> LENGTH: 60
<212> TYPE: DNA
<213> ORGANISM: Homo sapiens
<400> SEQUENCE: 8
tcttatattt cttcttactg gatcatacgg tcggaggggt ttgccgtgaa accggctgct 60

<210> SEQ ID NO 9
<211> LENGTH: 39
<212> TYPE: DNA
<213> ORGANISM: Homo sapiens
<400> SEQUENCE: 9
ggcttctccc gggcacagac ttcatctttt ctctcttat 39

<210> SEQ ID NO 10
<211> LENGTH: 30
<212> TYPE: DNA
<213> ORGANISM: Homo sapiens
<400> SEQUENCE: 10
ggatcatacg gtcggagggt ttgccgtgaa 30

SEQUENCE LISTING

<160> NUMBER OF SEQ ID NOS: 10

<210> SEQ ID NO 1
<211> LENGTH: 26
<212> TYPE: DNA
<213> ORGANISM: Homo sapiens

<400> SEQUENCE: 1
ttggacctcg tacagaagct aatacg                                        26

<210> SEQ ID NO 2
<211> LENGTH: 44
<212> TYPE: DNA
<213> ORGANISM: Homo sapiens

<400> SEQUENCE: 2
taatacgact cactatagag taagaagaaa tataagagcc acca                    44

<210> SEQ ID NO 3
<211> LENGTH: 29
<212> TYPE: DNA
<213> ORGANISM: Homo sapiens

<400> SEQUENCE: 3
cttcctactc aggctttatt caaagacca                                     29

<210> SEQ ID NO 4
<211> LENGTH: 38
<212> TYPE: DNA
<213> ORGANISM: Homo sapiens

<400> SEQUENCE: 4
taatacgact cactataggg aaataagaga gaaaagaa                           38

<210> SEQ ID NO 5
<211> LENGTH: 38
<212> TYPE: DNA
<213> ORGANISM: Homo sapiens

<400> SEQUENCE: 5 ttctttctc tcttatttcc ctatagtgag tcgtatta                            38

<210> SEQ ID NO 6
<211> LENGTH: 60
<212> TYPE: DNA
<213> ORGANISM: Homo sapiens

<400> SEQUENCE: 6
taatacgact cactataggg cggtcacccc agcagccggt gtctgtgccc gggagaagcc   60

<210> SEQ ID NO 7
<211> LENGTH: 60
<212> TYPE: DNA
<213> ORGANISM: Homo sapiens

<400> SEQUENCE: 7
ggcttctccc gggcacagac accggctgct ggggtgaccg ccctatagtg agtcgtatta   60

<210> SEQ ID NO 8
<211> LENGTH: 60
<212> TYPE: DNA
<213> ORGANISM: Homo sapiens

<400> SEQUENCE: 8

```
tcttatattt cttcttactg gatcatacgg tcggaggggt ttgccgtgaa accggctgct    60

<210> SEQ ID NO 9
<211> LENGTH: 39
<212> TYPE: DNA
<213> ORGANISM: Homo Sapiens

<400> SEQUENCE: 9
ggcttctccc gggcacagac ttcatctttt ctctcttat                          39

<210> SEQ ID NO 10
<211> LENGTH: 30
<212> TYPE: DNA
<213> ORGANISM: Homo sapiens

<400> SEQUENCE: 10
ggatcatacg gtcggagggt ttgccgtgaa                                    30
```

What is claimed is:

1. A method for in vitro selective translation of a desired protein, comprising:
   (a) providing a modified nucleic acid enzyme, including two catalytic half cores of a minimized 9DB1 deoxyribozyme split between nucleotides 35 and 39, wherein each half core includes a pendant assembly arm of nucleic acids extending therefrom and a separate, pendant binding arm extending therefrom of nucleic acids;
   (b) binding a nucleic acid ligand to each of the two assembly arms to form an intermediate;
   (c) binding the intermediate to (i) a first substrate of a strand of ribonucleic acids capped at one end, (ii) a second substrate of a second strand of ribonucleic acids having a 5' triphosphate region at one end and a region of polyadenylated nucleotides at the other end and wherein the second substrate has a region that codes for the desired protein, (iii) join the two catalytic half cores to form a catalytic core in order to form a ligated product complex; and
   (d) allowing the translation for the desired protein to proceed from the ligated product complex.

2. The method of claim 1, wherein the pendant binding arm extends from a strand of nucleic acids.

3. The method of claim 1, wherein the pendant binding arm extends from a segment of nucleic acids.

* * * * *